(12) United States Patent
Sim

(10) Patent No.: US 6,589,938 B2
(45) Date of Patent: Jul. 8, 2003

(54) USE OF ANGIOTENSIN I DERIVATIVES AS AN AGENT FOR THE TREATMENT AND PREVENTION OF INFARCTION-RELATED CARDIAC INJURIES AND DISORDERS

(75) Inventor: Meng Kwoon Sim, Singapore (SG)

(73) Assignee: National University of Singapore, Singapore (SG)

( * ) Notice: Subject to any disclaimer, the term of this patent is extended or adjusted under 35 U.S.C. 154(b) by 23 days.

(21) Appl. No.: 09/895,273

(22) Filed: Jun. 29, 2001

(65) Prior Publication Data

US 2003/0017989 A1 Jan. 23, 2003

(51) Int. Cl.$^7$ ................................................ A61K 38/00
(52) U.S. Cl. ........................................................ 514/15
(58) Field of Search ........................................... 514/15

(56) References Cited

U.S. PATENT DOCUMENTS

| | | | |
|---|---|---|---|
| 5,773,415 A | 6/1998 | Sim | 514/15 |
| 6,100,237 A | 8/2000 | Sim | 514/15 |

OTHER PUBLICATIONS

Tsai et al., Synthesis and Evaluation of [Des–Asp1]angiotensin I as a Precursor for [Des–Asp1]angiotensin II ("Angiotensin III"), J. Med. Chem. 18:1180–1183, 1975.*

Blair–West et al. (1971) *J. Clin. Endocrinal, Metab.* 32:575–578.
Tsai et al. (1975) *J. Med. Chem.* 18:1180–1183.
Sim and Chai (1996) *Br J. Pharmocol.* 117:1504–1506.
Sim and Radhakrishnan (1994) *Eur. J. Pharmacol.* 257:R1–R3.
Sim and Min (1998) *Int. J. Cardiol.* 63:223–227.
Min et al. (2000) *Regul. Peptides* 95:93–97.
DeMello et al. (2000) *Hypertension* 35:1183–1188.
Fishbein et al. (1978) *Am. J. Path.* 90:57–70.
Oh et al. (1993) *Circulation* 87:598–607.

* cited by examiner

*Primary Examiner*—Dwayne Jones
(74) *Attorney, Agent, or Firm*—Klarquist Sparkman, LLP

(57) ABSTRACT

The present invention relates generally to a method for the treatment and/or prophylaxis of infarction-related cardiac injuries and disorders. More particularly, the present invention contemplates a method for the treatment and/or prophylaxis of myocardial infarction and heart failure and/or related conditions. The method of the present invention is practised by the administration of a derivative of angiotensin I. In a preferred embodiment, the angiotensin I is des-Aspartate-angiotensin I. The present invention further contemplates compositions for use in the treatment and/or prophylaxis of infarction-related cardiac injuries and disorders such as but not limited to myocardial infarction and heart failure.

13 Claims, No Drawings

USE OF ANGIOTENSIN I DERIVATIVES AS AN AGENT FOR THE TREATMENT AND PREVENTION OF INFARCTION-RELATED CARDIAC INJURIES AND DISORDERS

FIELD OF THE INVENTION

The present invention relates to the use of angiotensin I derivatives, including des-Aspartate angiotensin I in the treatment and/or prevention of infarction-related cardiac injuries and disorders. More particularly, the present invention contemplates a method for the treatment and/or prevention of myocardial infarction, heart failure and/or related conditions. The present invention further contemplates compositions for use in the treatment and/or prophylaxis of infarction-related cardiac injuries and disorders such as but not limited to myocardial infarction and heart failure.

BACKGROUND OF THE INVENTION

Infarction or necrosis of part of the heart muscle can lead to various conditions including ischemia of cardiac tissue, angina, arrhythmia, cardiac hypertrophy, and heart failure. Extensive infarction or enlargement of infarction may result in cardiac arrest and death. Cardiac or myocardial infarction and related injuries and disorders contribute to significant morbidity and mortality in patients affected by such conditions.

Des-Aspartate angiotensin I (des-Asp-angiotensin I) is a nonapeptide produced from a decapeptide by the action of an aminopeptidase. The nonapeptide is produced from angiotensin I by enzymatic $NH_2$-terminal degradation (1). Des-Asp-angiotensin I is a substrate for plasma and pulmonary angiotensin converting enzyme (2). U.S. Pat. No. 5,773,415 discloses the attenuating effect of des-Asp-angiotensin I on experimentally induced non-infarction-related cardiac hypertrophy in rat. In U.S. Pat. No. 6,100,237, the use of des-Asp-angiotensin I as an anti-neointima and anti-arteriosclerotic agent is disclosed. It appears des-Asp-angiotensin I act on a specific indomethacin and losartan-sensitive subtype of angiotensin receptor $AT_1$ (3) to antagonize the pressor (4) and hypertrophic (5, 6) actions of angiotensin II. $AT_1$ is one of the two specific angiotensin receptors, the activation of which is related to the effect of angiotensin II on cardiac tissue (7).

The level of angiotensin II has been shown to increase after moycardial infarction (7). However, the precise role of angiotensin II in the pathology of myocardial infarction remains to be elucidated.

SUMMARY OF THE INVENTION

It has now been found surprisingly that angiotensin I derivatives, including des-Asp-angiotensin I is effective in the treatment and/or prevention of infarction-related cardiac injuries and disorders.

One aspect of the present invention therefore relates to a method for the treatment or prevention of an infarction-related cardiac injury or disorder, the method comprising administering an effective amount of a derivative of angiotensin I to a subject in need of such treatment or prevention. In one embodiment, the derivative of angiotensin I is des-Asp-angiotensin I.

Another aspect of the invention relates to use of a derivative of angiotensin I to treat or prevent an infarction-related cardiac injury or disorder. In another aspect, the invention relates to use of a derivative of angiotensin I in the manufacture of medicament for the treatment or prevention of an infarction-related cardiac injury or disorder. Still a further aspect of the present invention provides a composition comprising a derivative of angiotensin I and a pharmaceutically acceptable carrier for use in the treatment or prevention of an infarction-related cardiac injury or disorder. In another aspect, the present invention relates to a combination comprising a container, a derivative of angiotensin I or a pharmaceutical composition containing the same, and instructions for use of the derivative of angiotensin I or the composition containing the same for the treatment or prevention of an infarction-related cardiac injury or disorder. A kit is also provided which comprises a derivative of angiotensin I and instructions for use of the derivative of angiotensin I for the treatment or prevention of an infarction-related cardiac injury or disorder. In specific embodiments according to these aspects of the invention, the angiotensin I derivative is des-Asp-angiotensin I.

DETAILED DESCRIPTION OF THE PREFERRED EMBODIMENTS

The effect of des-Asp-angiotensin I on the infarct size and transmurality in the left ventricle of a rat following experimental myocardial infarction was determined and the present invention is predicated in part on the determination that a derivative of angiotensin I prevents or otherwise attenuates or decreases the infarct size and transmurality. Animal models for studying infarction-induced injuries and disorders, including small animals such as the rat are well accepted in the art (8). The inventors have therefore determined, surprisingly that a derivative of angiotensin I such as des-Asp-angiotensin I is capable of preventing or otherwise ameliorating infarction-related cardiac injuries and disorders.

Accordingly, one aspect of the present invention provides a method for the treatment and/or prevention of infarction-related injuries and disorders, the method comprising administering an effective amount of a derivative of angiotensin I.

An "effective amount" refers to an amount effective, at dosages and for periods of time necessary to achieve the desired therapeutic result, such as to prevent, inhibit or delay the onset of infarction-related injuries and disorders or ameliorate the symptoms of infarction related injuries and disorders. While the effective amount may vary according to various factors such as the disease state, age, sex, and weight of the individual in the case of a human patient, in one embodiment, the effective amount is about 1.8 mg/kg/day.

The term "infarction-related injuries and disorders" is used herein in its broadest sense and includes myocardial infarction and any and all injuries, disorders or conditions, induced by, following, or related to myocardial infarction, including, ischemia of cardiac tissue, angina, arrhythmia, remodeling cardiac hypertrophy, congestive heart failure, and cardiac arrest. Following infarction, unaffected heart cells will compensate for heart cells that have died by realigning (remodelling) and growing bigger in size (hypertrophy). Remodeling cardiac hypertrophy as that term is used is therefore intended to describe infarction-related hypertrophy and is to be distinguished from non-infarction-related hypertrophy. Persons skilled in the art will also appreciate that treatment of infarction related cardiac hypertrophy differs from the treatment of non-infarction-related cardiac hypertrophy. The former is treated mainly with angiotensin converting enzyme inhibitors such as captopril and angiotensin receptor blockers such as losartan, while any drug that lowers blood pressure may be used to treat non-infarction-related cardiac hypertrophy.

A "derivative of angiotensin I" refers to any mutant, fragment, part or portion of angiotensin I, including molecules comprising single or multiple amino acid substitutions, deletions and/or insertions to angiotensin I and which inhibits, reduces or otherwise interferes with the activity or function of angiotensin II, or homologue, analogue or chemical equivalent thereof which is functionally equivalent in that it inhibits, reduces or otherwise interferes with the activity or functioning of angiotensin II.

Insertional amino acid sequence derivatives are those which include an addition of one or more amino acid residues. The addition may be introduced into a predetermined site or by random insertion with suitable screening of the resulting products. An amino acid insertional derivative of angiotensin I may include amino and/or carboxyl terminal fusions as well as intra-sequence insertions of single or multiple amino acids. Deletional derivatives are characterized by the removal of one or more amino acids from the sequence. Substitutional amino acid derivatives are those in which at least one residue in the sequence has been removed and a different residue inserted in its place.

A homologue of an angiotensin I derivative includes functionally, structurally or stereochemically similar polypeptides, for example from other species, such as livestock animals and laboratory test animals, including rodents and primates.

An analogue of an angiotensin I derivative includes a mimotope, or peptide or analogue mimetic and includes molecules which contain non-naturally occurring amino acids as well as molecules which do not contain amino acids but nevertheless behaves as a functional equivalent. Analogues contemplated herein include modifications to side chains, including deglycosylation or glycosylation, incorporation of unnatural amino acids and/or their derivatives during peptide synthesis and the use of crosslinkers and other methods which impose conformational constraints on the peptide molecule. Analogues also include angiotensin I derivative coupled directly or indirectly to at least one modifying group while retaining the functionality of the derivative. Such modifications are well known in the art and include, for example, a derivative modified to alter a pharmacokinetic property, such as in vivo stability, bioavailability or half-life. The derivative may also be coupled to an additional therapeutic moiety or to a detectable substance.

Examples of unnatural amino acids and/or their derivatives which may be incorporated during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilize 3D conformations, using homo-bifunctional crosslinkers such as the bifunctional imido esters having $(CH_2)_n$ spacer groups wherein n=1 to 6, glutaraldehyde, N-hydroxysuccinimide esters and hetero-bifunctional reagents which usually contain an amino-reactive moiety such as N-hydroxysuccinimide and another group specific-reactive moiety.

These types of modifications may be important to stabilize a derivative of angiotensin I, including des-Asp-angiotensin I. This may be important, for example, in the manufacture of a therapeutic composition or if angiotensin I derivative is used in detection assays. Examples of unnatural amino acids that may be incorporated are presented in Table 1.

TABLE 1

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nnmva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-α-aminobutyrate | Mgabu |
| D-α-methylalanine | Dmala | α-methylcyclohexylalanine | Mchexa |
| D-α-methylarginine | Dmarg | α-methylcylopentylalanine | Mcpen |
| D-α-methylasparagine | Dmasn | α-methyl-α-napthylalamine | Manap |

TABLE 1-continued

| Non-conventional amino acid | Code | Non-conventional amino acid | Code |
|---|---|---|---|
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | morn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-α-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcper |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| α-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L- -methylarginine | Marg | L-α-methylasparagine | Masn |
| L- -methylaspartate | Masp | L-α-methyl-t-butylglycine | Mtbug |
| L- -methylcysteine | Mcys | L-methylethylglycine | Metg |
| L- -methylglutamine | Mgln | L-α-methylglutamate | Mglu |
| L- -methylhistidine | Mhis | L-α-methylhomophenylalanine | Mhphe |
| L- -methylisoleucine | Mile | N-(2-methylthioethyl)glycine | Nmet |
| L- -methylleucine | Mleu | L-α-methyllysine | Mlys |
| L- -methylmethionine | Mmet | L-α-methylnorleucine | Mnle |
| L- -methylnorvaline | Mnva | L-α-methylornithine | Morn |
| L- -methylphenylalanine | Mphe | L-α-methylproline | Mpro |
| L- -methylserine | Mser | L-α-methylthreonine | Mthr |
| L- -methyltryptophan | Mtrp | L-α-methyltyrosine | Mtyr |
| L- -methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

A chemical equivalent of an angiotensin I derivative shares conformational or functional similarities and may not necessarily be derived from the derivative of angiotensin I. A chemical equivalent may be specifically designed to mimic certain physiochemical properties of a derivative of angiotensin I. Chemical equivalents may be chemically synthesized or may be detected following, for example, natural product screening of candidate compounds which can inhibit, reduce or otherwise interfere with the activity, or functioning of angiotensin II using assays described below.

A derivative of angiotensin I may readily be made using synthetic techniques well known in the art, such as solid phase peptide synthesis and the like, or by recombinant DNA manipulations. Techniques for making substitution mutations at predetermined sites in DNA having known or partially known sequence are well known and include, for example, M13 mutagenesis. The manipulation of DNA sequence to produce variant proteins, which manifest as substitutional, insertional or deletional variants are conveniently described, for example, in Sambrook et al. (9).

A derivative of angiotensin I may be readily identified, for example by its ability to act as an agonist on an indomethacin-sensitive angiotensin receptor or its ability to induce relaxation of a pre-contracted cardiac end of a rabbit pulmonary artery or its ability to attenuate angiotensin II-induced hypertrophy in cultured rat neonatal cardiomyocytes or its ability to attenuate the angiotensin II-induced hyperplasia in cultured rat aortic smooth muscle cells.

A preferred derivative of angiotensin I is des-Asp-angiotensin I, or derivative, homologue, analogue or chemical equivalent thereof. The term derivative in this context has the same meaning as used in the context of angiotensin I as described above. Similarly, the terms homologue, analogue and chemical equivalent as used in this context has the same meaning as described above for angiotensin I derivative generally.

It is well known in the art that modifications and changes can be made to the structure of a peptide without substantially altering the biological function of that peptide. To this end, where des-Asp-angiotensin I is derivatized by amino acid substitution, the amino acids are generally replaced by other amino acids having like properties, such as hydrophobicity, hydrophilicity, electronegativity, size, and the like. Amino acid substitutions are typically of single residues.

Amino acid insertions will usually be in the order of about 1-9 amino acid residues and deletions will range from about 1-9 residues.

Reference herein to angiotensin I derivative and des-Asp-angiotensin I should be read as including reference to all functionally equivalent forms, including, by way of example, isoforms, monomeric, dimeric and multimeric forms.

An effective amount of the derivative of angiotensin I such as but not limited to des-Asp-angiotensin I or a derivative, homologue, analogue or chemical equivalent thereof or a pharmaceutical composition containing the same, as described below, is administered to a subject, such as a human patient, via any acceptable method known in the art, either singly or in combination with other pharmaceutical agents such as captopril or other angiotensin converting enzyme inhibitors or angiotensin receptor antagonists such as losartan. The compound or composition may be administered orally, by suppository, or parenterally (e.g. intramuscularly, intravenously, subcutaneously or intradermally), and in the form of either solid or liquid dosage including tablets, suspensions, or solutions, as is discussed in more detail below. The administration may be conducted in single dosage form with continuous therapy or in single dose therapy ad libitum.

Useful pharmaceutical carriers for the preparation of the pharmaceutical compositions hereof can be solids, liquids or mixtures thereof; thus, the compositions can take the form of tablets, pills, capsules, powders, enterically coated or other protected formulations, sustained release formulations, erodible formulations, implantable devices or components thereof, microsphere formulations, solutions, suspensions, elixirs, aerosols and the like.

Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Other pharmaceutically acceptable carriers will be apparent to one skilled in the art. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The composition may be subjected to conventional pharmaceutical expedients such as sterilization and may contain conventional pharmaceutical additives such as preservatives, stabilizing agents, wetting or emulsifying agents, salts for adjusting osmotic pressure, buffers and the like. Suitable pharmaceutical carriers and their formulations are described in Martin, "Remington's Pharmaceutical Sciences", 15$^{th}$ Ed.; Mack Publishing Co., Easton (1975); see, e.g. pp. 1405–1412 and pp 1461–1487. Such compositions will, in general, contain an effective amount of the active compound together with a suitable amount of carrier so as to prepare the proper dosage form for proper administration to the host.

The methods of the present invention may be practiced when the relief of symptoms is specifically required or to prevent imminent threat of an infarction related cardiac injury or disorder. For example, angina that occurs at rest can indicate an imminent myocardial infarction and administration of angiotensin I derivative such as des-Asp-angiotensin to a person experiencing such symptom may prevent myocardical infarction in that patient. The method of the invention may also be effectively practiced as a continuous or prophylactic treatment.

In the practice of the therapeutic methods of the invention, the particular dosage of pharmaceutical composition to be administered to the subject will depend on a variety of consideration including the stage of the disease or condition, the severity thereof, the schedule of administration, the age and physical characteristics of the subject, and so forth. Proper dosages may be established using clinical approaches familiar to the medicinal arts.

An angiotensin I derivative, including des-Asp-angiotensin I or a pharmaceutical composition containing the same may be provided, sold or otherwise made available, including to patients, physicians and pharmacists, in a container together with instructions for use of the derivative or composition in the treatment or prevention of an infarction related cardiac injury or disorder. One aspect of the invention therefore relates to any such combination. It will be understood that the container in any such combination will be suitable for storing the derivative of angiotensin I or the composition containing the same. Another aspect of the invention relates to a kit comprising a derivative of angiotensin I and instructions for use of the derivative of angiotensin I for the treatment or prevention of an infarction related cardiac injury or disorder. In one embodiment, the kit may further include a pharmaceutically acceptable carrier. In different embodiments of these aspects of the invention, the derivative of angiotensin I may be des-Asp-angiotensin I or derivative, homologue, analogue or chemical equivalent thereof.

Although the present invention is particularly exemplified herein in relation to rats, it is understood that the present invention extends to the use of angiotensin I derivatives in any mammal subject including, but not limited to, humans, mice, rabbits, livestock animals and primates.

The present invention is further described in the following non-limiting Examples.

EXAMPLE 1

Source of Materials

Des-Asp-angiotensin I was obtained from Bachem (Dubendorf, Switzerland). Des-Aspartate-angiotensin I can be prepared by techniques well known in the art. Adult Sprague Dawley rats (SD, 250–300 g) were obtained from the Animal Center, National University of Singapore.

EXAMPLE 2

Induction of Cardiac Infarction

The experimental protocol for induction of cardiac infarction by coronary occlusion and reperfusion in rats was carried out as described by Oh et al. (10). Briefly, each rat was anaesthetized with 7% w/v chloral hydrate (0.4 g/kg, i.p.). Each anaesthetised animal was intubated and ventilated with a rodent ventilator. Under a dissecting microscope, a left thoracotomy was performed in the fourth intercostal space, and the pericardium open. The left coronary artery was encircled with a curved needle and a silk suture. The left coronary artery was ligated for 45 minutes, followed by reperfusion. In sham-operated animals, the left coronary artery was not ligated. The chest was closed in layers and the pneumothorax evacuated.

EXAMPLE 3

Treatment With Des-Asp-Angiotensin I and Measurement of Infarct Size and Transmurality Following the surgery, each animal was placed in a cage. The animals had access to water and rat chow ad libitum. The animals were randomly divided into the control group and treatment group. Each group consisted of 7 animals. The treatment group was orally administered 381 nmoles/kg/day of des-Asp-angiotensin I (dissolved in 1 ml water) for 14 days. The control group was similarly administered an equivalent volume of water. The experiment was repeated with the following doses of des-Asp-angiotensin I: 762, 1524, and 3096 nmoles/kg/day.

On the fourteenth day following surgery, animals were anaesthetised as before. Rats were ventilated as before and the thorax was opened. A polyethylene catheter (PE 200) was introduced into the left ventricle (via the left atrial appendage) and another into the descending aorta retrogradely. The heart was arrested with 2 ml injection of saturated KCl solution into the right atrium. After aortic perfusion with heparinized saline (10,000 units/L) for 3 minutes to wash out the blood, the myocardium was perfused retrogradely from the aorta with 4% phosphate-buffered paraformaldehyde at a constant pressure of 60 mm Hg for 20 minutes. The right atrium and pulmonary artery were opened to decompress the right ventricle during fixation. The left ventricle intracavity pressure was maintained at 10 mm Hg by use of the cathether introduced via the left atrial appendage.

After hardening, the heart was excised and postfixed in 4% paraformaldehyde for 24 hours. Following postfixing, the atria and adhensions were carefully dissected away and the right and left ventricles were separated, the interventricular septum being included with the left ventricle. The left ventricle was processed for paraffin embedment. Transverse serial sections of 40 $\mu$m thick were cut from the apex of the ventricle to its base. Every section at 1 mm intervals was mounted and stained with Milligan's trichrome. The infracted tissue (infarct scar) was stained blue. Two sections, taken at 5 and 6 mm, respectively, from the apex of each ventricle were used for morphometric determination of the infarct scar area and transmurality. The morphometry system consisted of a BX40 light microscope (Olympus, Japan) fitted with a KYF55B colour video camera (JVC, Japan) and a Pentium 166 MHz/MKX microcomputer (Datamini, Singapore) installed with an image Pro Plus 3.0 System (Media Cybernetics, USA) for Windows 95™. The infarct scar area, infarct area (which measured the scar and the surrounding surviving ventricular tissue) were determined in mm2. Transmurality is equal to the infarct scar area divided by infarct area.

EXAMPLE 4

Effect of des-Asp-angiotensin

The results of the study are summarized in Table 2 Data were expressed as mean±SEM. Significant differences were determined by one way ANOVA and post hoc Newman Kleuf test. The accepted level of significance was p<0.05. Des-Asp-angiotensin I is an effective agent in attenuating the infarct size area and transmurality in experimentally-induced myocardial infracted rats. The effect was dose dependent and significant anti-infarction action was brought about by an oral dose of 1524 nmoles/kg/day.

TABLE 2

Effects of des-aspartate-angiotensin I on infarct size area and transmurality in experimentally-infarcted rats

| Dose (nmole/kg/day) for 14 days) | Infarct Scar Area (mm$^2$) | | Transmurality (%) | |
|---|---|---|---|---|
| | Control | Treated | Control | Treated |
| 381 | 6.61 ± 0.24 | 5.85 ± 0.25 | 34.33 ± 2.26 | 32.93 ± 1.94 |
| 762 | 6.20 ± 0.50 | 5.60 ± 0.30 | 37.10 ± 3.60 | 33.70 ± 3.40 |
| 1524 | 6.62 ± 0.31 | 5.11 ± 0.54* | 32.41 ± 2.09 | 24.67 ± 2.37* |
| 3096 | 6.60 ± 0.23 | 5.86 ± 0.20* | 34.34 ± 2.24 | 31.26 ± 1.53* |

Values of Infarct Scar Area and Transmurality were mean ± SEM obtained from 7 individual rats. *Significantly different (p < 0.05) from the corresponding value of the Control.

All references cited herein are fully incorporated by reference. Having now described the invention, it will be understood by those skilled in the art that various modifications can be made to the described embodiments without departing from the scope and spirit of the invention. Such modifications are intended to be within the scope of the invention.

Bibliography

1. Blair-West et al. (1971) *J. Clint. Endocrinal. Metal.* 32:575–578
2. Tsai et al. (1975) *J. Med. Chem.* 18:1180–1183
3. Sim and Chai (1996) *Br J. Pharmocol.* 117:1504–1506
4. Sim and Radhakrishnan (1994) *Eur. J. Pharmacol.* 257:R1–R3
5. Sim and Min (1998) *Int. J. Cardiol.* 63:223–227
6. Min et al. (2000) *Regul. Peptides* 95:93–97
7. DeMello et al. (2000) *Hypertension* 35:1183–1188.
8. Fishbein et al. (1978) *Am. J. Path.* 90:57–70.
9. Sambrook et al. (1989). Cloning. A laboratory manual. Cold Spring Harbour Laboratory, Cold Spring Harbour, N.Y.
10. Oh et al. (1993). *Circulation* 87:598–607.

What is claimed is:

1. A method for the treatment or prevention of an infarction-related cardiac injury or disorder, comprising administering to a subject in need of such treatment or prevention an effective amount of a derivative of angiotensin I.

2. The method according to claim 1 wherein the infarction-related cardiac injury or disorder is myocardial infarction, ischemia of cardiac tissue, angina, arrhythmia, remodeling cardiac hypertrophy, congestive heart failure or cardiac arrest.

3. The method according to claim 2 wherein the derivative of angiotensin I is des-Asp-angiotensin I or a derivative, homologue, analogue or chemical equivalent thereof.

4. The method according to claim 3 wherein the derivative of angiotensin I is des-Asp-angiotensin I.

5. The method according to 4 wherein the subject is a human patient.

6. The method according to claim 5 wherein the effective amount is about 1.8 mg/kg/day.

7. The method of claim 5 wherein said des-Asp-angiotensin I is administered orally.

8. The method according to claim 5 wherein said des-Asp-angiotensin I is administered by suppository.

9. The method according to claim 5 wherein said des-Asp-angiotensin I is administered parenterally.

10. The method according to claim 5 wherein said des-Asp-angiotensin I is administered in the form of a solid dosage.

11. The method according to claim 5 wherein said des-Asp-angiotensin I is administered in the form of a liquid dosage.

12. The method according to claim 5 wherein said des-Asp-angiotensin I is administered in combination with another pharmaceutical agent.

13. The method according to claim 12 wherein the pharmaceutical agent is an angiotensin converting enzyme inhibitor or angiotensin receptor antagonist.

* * * * *